(12) United States Patent
Ternström

(10) Patent No.: US 6,676,639 B1
(45) Date of Patent: Jan. 13, 2004

(54) CANNULA

(75) Inventor: Staffan Ternström, Varberg (SE)

(73) Assignee: Safe Conduct AB, Varberg (SE)

( * ) Notice: Subject to any disclaimer, the term of this patent is extended or adjusted under 35 U.S.C. 154(b) by 0 days.

(21) Appl. No.: 09/913,030

(22) PCT Filed: Feb. 10, 2000

(86) PCT No.: PCT/SE00/00272

§ 371 (c)(1),
(2), (4) Date: Aug. 10, 2001

(87) PCT Pub. No.: WO00/47117

PCT Pub. Date: Aug. 17, 2000

(30) Foreign Application Priority Data

Feb. 10, 1999 (SE) .................................. 9900454

(51) Int. Cl.⁷ ................................................ A61M 5/32
(52) U.S. Cl. ...................................................... 604/174
(58) Field of Search ................................. 604/174, 175, 604/178, 164, 165, 167, 110, 113, 198, 105

(56) References Cited

U.S. PATENT DOCUMENTS

| 3,044,461 A | 7/1962 | Murdock |
| 3,789,852 A | 2/1974 | Kim et al. |
| 5,139,511 A | 8/1992 | Gill et al. |
| 5,279,564 A | 1/1994 | Taylor |
| 5,312,417 A | 5/1994 | Wilk |
| 5,391,156 A | 2/1995 | Hildwein et al. |
| 5,545,179 A | 8/1996 | Williamson, IV |
| 5,634,911 A | 6/1997 | Hermann et al. |
| 5,634,937 A | 6/1997 | Mollenauer et al. |
| 5,707,359 A | 1/1998 | Bufalini |
| 5,741,234 A | 4/1998 | Aboul-Hosn |

*Primary Examiner*—Manuel Mendez
(74) *Attorney, Agent, or Firm*—Burns, Doane, Swecker & Mathis, L.L.P.

(57) ABSTRACT

The present invention refers to a device, such as a trocar intended to penetrate a body wall in endoscopic surgery to establish a passageway allowing insertion therethrough of surgical instruments, and comprising a tubular sleeve extending through the passageway and having one proximal and one distal end. The device in accordance with the invention is characterized in that the distal end is arranged to be contracted such that it assumes dimensions not exceeding the surgical orifice to allow said end to be introduced into said orifice, and thereafter to expand when applied in position such that is assumes downwards gradually increasing dimensions transversely exceeding the dimensions of the device at the place of the surgical orifice, whereby a funnel-shaped distal end is formed.

27 Claims, 5 Drawing Sheets

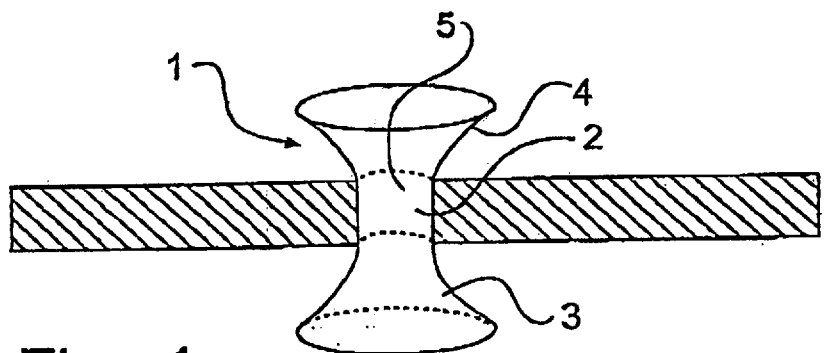
Fig. 1
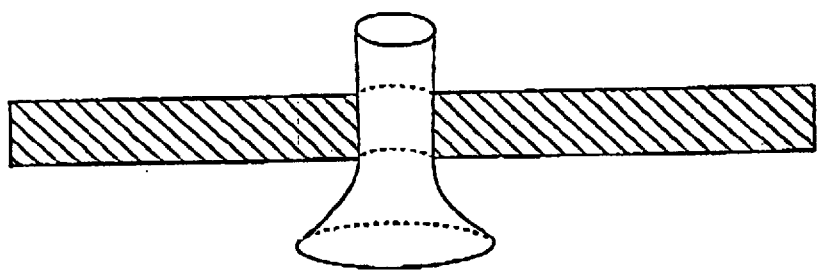
Fig. 2
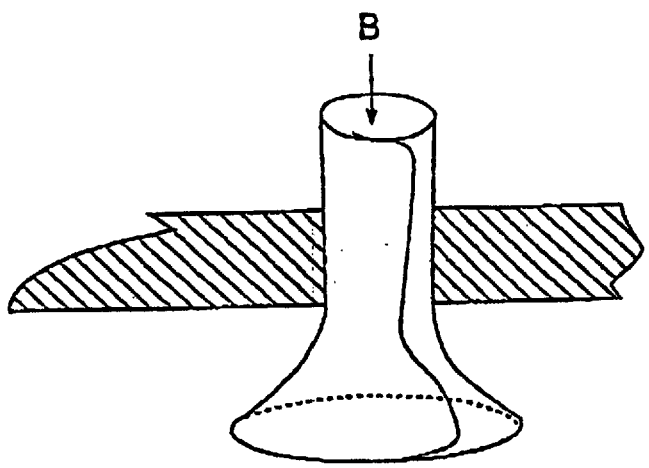 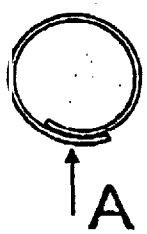
Fig. 3A    Fig. 3B

CANNULA

TECHNICAL FIELD

The present invention concerns a device, such as a trocar, which is intended to penetrate a human body wall in endoscopic surgical operations to establish a passageway for insertion of surgical instruments and extraction of specimens therethrough, and which comprises a through-passage sleeve having one proximal and one distal end.

BACKGROUND

Laparoscopic surgery, also known as keyhole surgery, has gained in importance in general surgery, gynecological surgery and urological surgery. The advantages compared with conventional surgery methods are considerable, both to the patient and to society. In the case of laparoscopic surgery operations small-dimension puncture orifices are made in the abdominal wall, through which trocars (tubular sleeves) of the kind mentioned in the introduction are inserted, and the laparoscope instrument as well as one or several operational instruments are introduced through the trocars. As a rule, the abdomen is inflated with gas, which increases the abdominal volume considerably, thereby providing an overall view and assessibility. The image of the surgical area is transmitted to a monitor and the diseased organ is isolated and separated from the surrounding tissue with the aid of the operational instruments. The surgical technique, the instruments, and other equipment for this purpose are already well known and highly developed. The specimen (the organ, the surgically removed tissue) must then be removed from the patient's abdomen. When small size, the specimen may be pulled out directly through the trocar, but when it is larger, it is necessary to first fragmentise it into smaller pieces.

Many varieties of trocars are already known. One problem encountered in many of them is the difficulty in making them stay in place, a problem which may be solved by stitching projecting flanges on the trocar to the body wall. Another alternative is to expand the inserted distal end. This solution is known from e.g. U.S. Pat. No. 5,545,179, which document shows a trocar the distal end of which may be inflated like a balloon about the tube.

Under certain circumstances it is also useful if the trocar can be used to lift and abdominal wall (the wall of the abdominal cavity), above all in the case of so called gas-free laparoscopy. Special tools, known as laparolifters, have been developed for this purpose.

Another problem found in many trocars is the difficulty of imparting to the instruments that are introduced via the trocar as efficient movability and accessibility properties as possible. These objects are achieved in accordance with the prior-art technology by manufacturing the trocar from a soft and pliable material, thereby allowing the distal trocar end to shape itself in conformity with the instrument. Trocars of this kind are known from e.g. U.S. Pat. No. 5,634,911 and U.S. Pat. No. 5,391,156.

Furthermore, trocars are known wherein the tube diameters is changeable, thus able to be expanded or contracted. Trocars of this kind are known from U.S. Pat. No. 3,789,852, which describes a trocar the peripheral surface of which is arranged to overlap, and from U.S. Pat. No. 5,139,511.

One problem that prior-art trocars have so far failed to solve is the difficulty connected with the extraction of the specimen. The specimen or pieces of the specimen are often extracted directly through the trocar by means of a pair of tongs or the like. It is then desirable that it be possible to extract as large pieces as possible for speed efficiency and to reduce as far as possible the need to fragmentise the specimens. In addition, it is of course desirable that the through-passage orifices are as small as possible to minimise the surgical intervention and the patient's discomfort. Consequently, it is desirable that the trocar is designed to be of assistance in guiding the specimen correctly as the latter is being introduced into the trocar tube, in order to prevent the specimen from sticking, from assuming an oblique position or the like. It is likewise desirable that the specimen be compressed as far as possible and be contracted so as to assume a spool-shape or similar configuration.

These and other problems are connected not only with laparoscopic surgery but under similar conditions with essentially all endoscopic surgery, including thorascopy surgery (laparoscopic surgery in the thorax cavity).

OBJECT OF THE INVENTION

Consequently, one object of the present invention is to provide a device, which facilitates the extraction of specimens while at the same time it is comparatively firmly fixed to the body-cavity wall, thus at least partly solving the above described problems from which prior-art solutions suffer.

This object is achieved by means of a trocar of the kind defined in the appended claims.

SUMMARY OF THE INVENTION

The invention concerns a trocar intended to penetrate a body wall in endoscopic surgery to establish a passageway allowing insertion therethrough of surgical instruments, and comprising a tubular sleeve having one proximal and one distal end. The device in accordance with the invention is characterised in that the distal end is arranged to be contracted such that it assumes transverse dimensions not exceeding the surgical orifice to allow said end to be introduced into said orifice, and thereafter to expand when applied in position such that it assumes downwards gradually increasing dimensions transversely exceeding the dimensions of the device at the place of the surgical orifice, whereby a funnel-shaped distal end is formed.

Through the funnel-shaped end, the specimens to be extracted are guided straight into the tube while at the same time they are suitable orientated for extraction. The gradual contraction or size reduction of the distal trocar end in the direction towards the tube proper causes some squeezing-together also of the specimen, whereby the latter is compressed while at the same time no edges exist on which the specimen may be stuck while passing. In this manner extraction of specimens is highly facilitated and larger-size specimen pieces may be extracted and/or smaller trocars be used. In addition, the funnel-shaped configuration of the trocar end contributes to maintaining the device in position in the surgical orifice in the body wall.

In order to further strengthen the retaining capacity of the device, the latter could also be provided with locking means, such as a rocker element, which locks the trocar in the inserted operative position of the latter. A trocar of this kind represents a preferred embodiment of the device in accordance with the invention.

In accordance with another preferred embodiment of the invention at least the distal end of the trocar is made from a resilient material which in itself tends to assume the expanded position. In this manner, the device is easily inserted while in its contracted position, while the distal end, when released, assumes its expanded position. The latter position is then maintained automatically owing to the nature of the material. When the device is to be extracted, the extraction force will again compress the distal end, overriding the resiliency of the material.

Preferably, at least the narrowest part of the device is yieldable and thus has a variable size in the transverse direction. As a result, specimens of a slightly too large size may be pulled through the device, since in this case the tube will widen slightly. This arrangement causes the specimen to be compressed further while at the same time the sensitivity of the device to too large specimens diminishes.

Other advantageous pecularities of the invention will appear from the following description of embodiment of the invention.

BRIEF DESCRIPTION OF THE DRAWINGS

In the attached drawings:

FIG. 1 illustrates a first embodiment of a device in accordance with the invention, the device assuming an expanded position;

FIG. 2 illustrates a second embodiment of a device in accordance with the invention, the device assuming an expanded position;

FIGS. 3a and 3b illustrates a third embodiment of a device in accordance with the invention;

DESCRIPTION OF PREFERRED EMBODIMENTS

Figure 4:
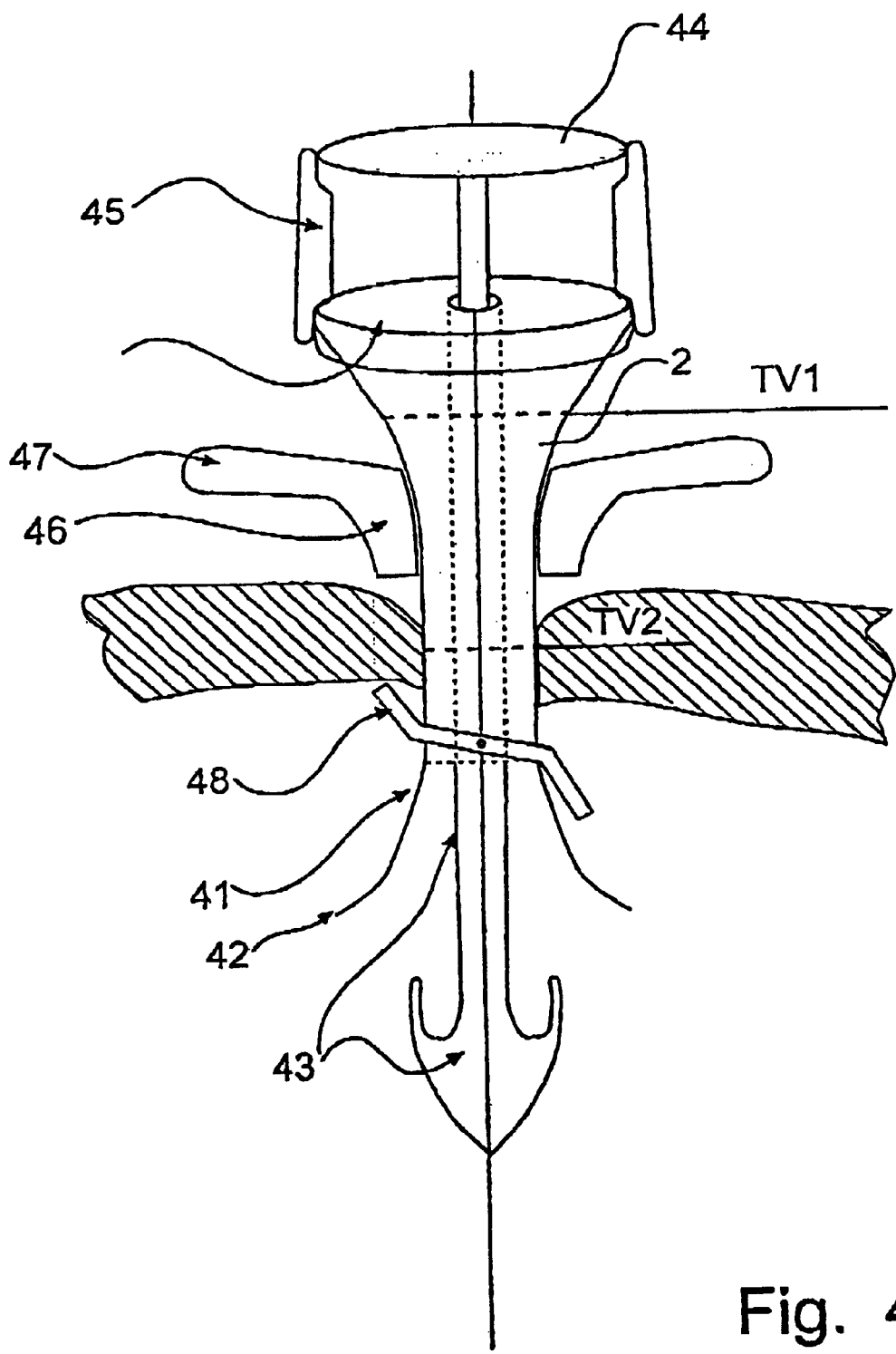
FIG. 4 is a cross-sectional view through a fourth embodiment of the device in accordance with the invention, the device assuming an expanded, dilated position.

For exemplifying purposes the invention will be described in the following with reference to one embodiment thereof. In FIG. 1 is shown a first embodiment of a trocar in accordance with the invention. The trocar 1 in this case comprises a tubular sleeve 2 having a distal end 3, which is designed to be passed through the body wall, and a proximal end 4 intended to remain exteriorly of the patient's body.

In addition, the distal end 3 is contractable, allowing it to assume transverse dimensions not exceeding those of the surgical orifice through which said trocar end is to be inserted, and to thereafter expand, when in its position of application, until it assumes a downwards gradually increasing transverse extension exceeding the extension of the trocar in the area of the surgical orifice. In this manner a funnel-shaped distal trocar end is obtained. The expandability may be obtained by the use of a comparatively rigid material having resilient properties such that the material in itself tends to assume the expanded position. The end may then be squeezed together and be maintained in that condition during the insertion. When the end is then released it automatically resumes the expanded condition. Upon extraction of the trocar, the end may either be contracted prior to extraction, or be automatically compressed when being pulled upwards through the orifice.

In addition, the trocar preferably comprises a non-return valve 5 or the like in order to make it gas-tight, which is a desirable feature when the trocar is used in surgery with gas. Valves of this kind are well known within the technical field concerned and will not be described in closer detail herein. It is, however, likewise possible to use the trocar in surgical operations where gas is not used and no valve is needed.

A trocar in accordance with the first embodiment of the invention, shown in FIG. 1, is also configured with a funnel-shaped upper end, giving the trocar as a whole an hourglass configuration when in its applied position. This shape facilitates insertion of tools through the trocar, since it guides the tool towards the orifice. In addition, the shape keeps the trocar in place, restraining it from being moved upwards as well as downwards.

It is of course likewise possible to configure the proximal end otherwise than shown and to use any one of a number of conventional methods to prevent if from sliding down through the orifice. One such alternative configuration is shown by the inventive embodiment illustrated in FIG. 2, according to which the distal end is formed with an essentially constant diameter size.

FIGS. 3a and 3b show a third embodiment of a trocar in accordance with the invention. According to this embodiment the trocar has the same shape as the trocar of the second embodiment, with the exception that in this case at least the most narrow part of the trocar, viz. the tubular sleeve 2, is yieldable and consequently capable of modifying its transverse dimensions. This feature may be obtained for instance by the use of a material that is at least somewhat resilient, allowing it to dilate when exposed to a pressure from within. Alternatively, the peripheral wall of the trocar is divided as shown in FIG. 3 and arranged somewhat overlapping. Preferably, the material is resilient and tends to assume a predetermined normal position, whereby after being dilated, the trocar resumes its original condition.

The trocar in accordance with the invention preferably is formed, at least on its inner face, with a smooth material with low sliding resistance, preferably a plastics material. This facilitates extraction of the specimens even more.

FIG. 4 shows a fourth embodiment of the trocar in accordance with the invention. According to this embodiment the sleeve is formed at its lower end with a number of tongues 41 with inherent resilience urging the tongues outwards. In addition, the tongues preferably have end portions 42 that are bent somewhat outwards, a configuration that furthers displacement of the specimen in the direction towards the trocar. In their position of insertion, the tongues are brought close together and are maintained in close relationship for example by means of a particular insertion tool 43, a so called mandrel or obturator. This obturator, shown in more detail in FIG. 5, preferably is formed with a slightly peaked tip 51 with a recess 52 for reception of the tongues. In addition, the obturator comprises an through rod 53, which extends through the trocar. At its opposite end, which protrudes from the trocar, the rod 53 preferably is connected to a handle 44. Owing to this arrangement, when the trocar is being prepared for insertion the obturator may be applied in a position wherein it locks the tongues in their close relationship position. Preferably, the obturator is locked in this position, for example by means of a spacer member 45 applied between the handle 44 and the upper part of the trocar. In this manner the handle 44 may be used to force the trocar through the surgical orifice in the body wall without any risk that the tongues are released outwards. Once the trocar is inserted to a sufficient depth the obturator is freed, whereupon the handle is depressed somewhat further. This movement release the tongues, which lock the trocar in place, and the obturator may then be pulled upwards through the trocar.

Furthermore, the trocar may advantageously be provided with a removable locking ring 46 or similar locking means to be applied at the upper part of the trocar, closest to the body wall, in order to prevent the trocar from being pushed downwards further. Also, this locking means may be provided with a grasping means 47, which could be helpful in the ultimate pressing-down of the obturator.

Figures 5, 6:
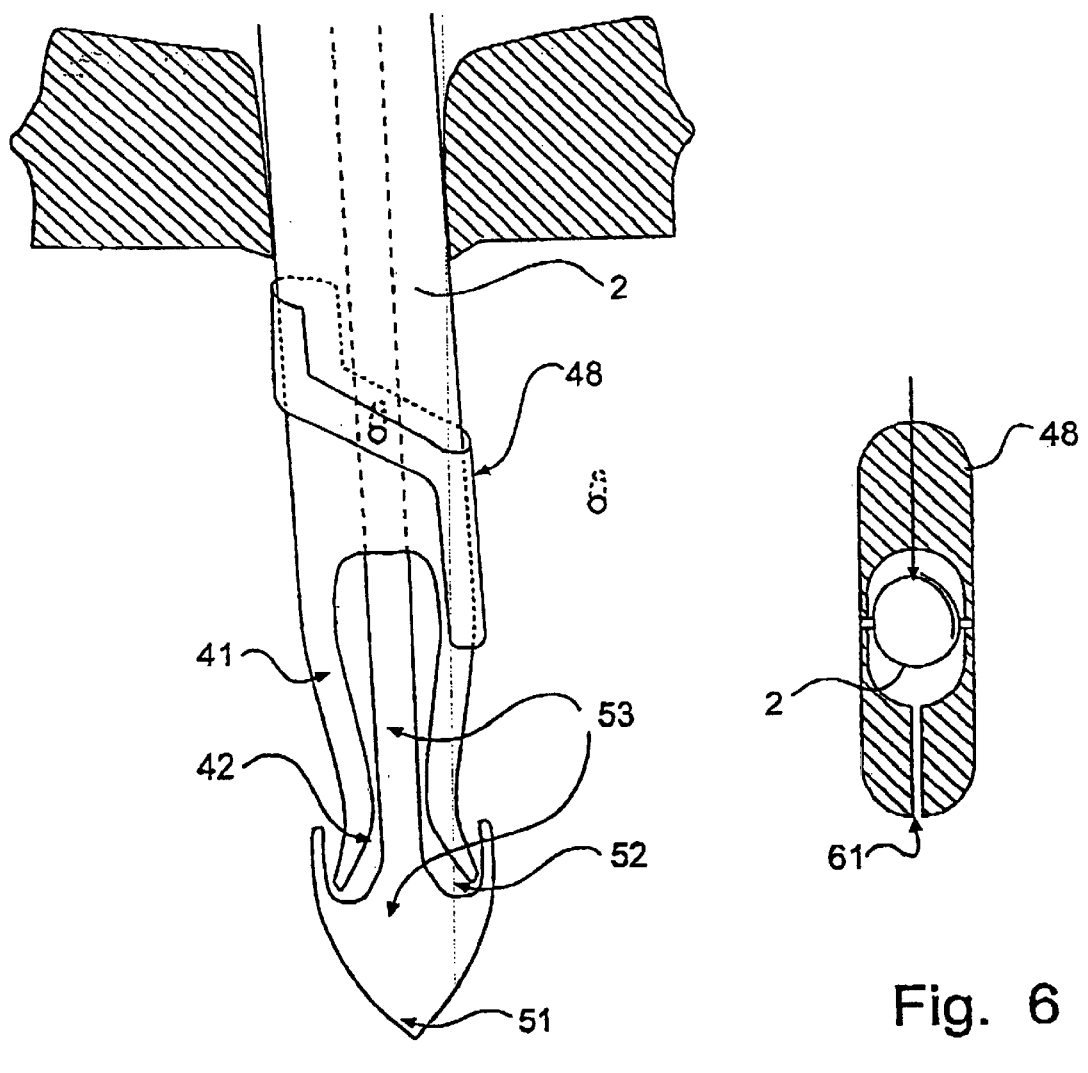
FIG. 5 illustrates a part of the device of FIG. 4 in a contracted condition.
FIG. 6 illustrates the tiltable rocker element of FIG. 4 in a view from above.

Preferably, the trocar is provided with a further locking means serving to prevent the trocar from being pulled upwards and thus to strengthen the effect provided by the expanding lower orifice. This feature is particularly advantageous when the trocar is to be used in laparoscopic surgery operations and the like when no gas is used, in which case the trocar may be used to lift the body wall. A locking means for this purpose may be designed as a rocker element 48. Preferably, the rocker element is rotationally mounted on the trocar sleeve and pivotal between an inner position, wherein it extends essentially along the trocar sleeve lengthwise (see FIG. 5), and an outer position, wherein it protrudes beyond the sleeve transversely (see FIG. 4). To shift the rocker element between the inner and outer positions and also to retain it in a chosen position, either additional surgical instruments such as tongues and the like may be used, or else integrated manoeuvring means, such as threads, which project above the trocar and with the aid of which the ends of the rocker element may be pulled in different directions. Preferably, the rocker element is also formed with a slit 61 or the like as shown in FIG. 6 in order not to prevent the dilation of the trocar sleeve 2. Other varieties of this rocker-element lock are of course conceivable, wherein a lock part is provided on the trocar sleeve and may be shifted between a position, wherein it does not essentially protrude from the sleeve and position wherein it does. A rocker-element lock of this kind could also advantageously be used on trocars generally, i.e. trocars that are not formed with an expanding lower part.

Instead of having expanding tongues the trocar could of course be configured with a continuous, funnel-shaped surface. For insertion through the surgical orifice formed in the body wall, the distal end preferably is compressed by exertion of pressure on a number of spots located around its peripheral wall, urging them towards the trocar centre axis. These contraction spots preferably are at least four in number and equidistantly spaced around the circumference. The contracted position is then locked by means of a sleeve 6 or the like, or an obturator like the one described above. The sleeve 6 is applied onto the distal end from below and preferably it is connected to a manoeuvring rod 7 and has a diameter smaller than the smallest inner diameter of the trocar. In use the contracted distal end thus may be inserted through the surgical orifice made for instance in the abdominal wall. Once the trocar is in position, the sleeve 6 is depressed further by means of the manoeuvring rod 7, whereby it separates from the distal end. Owing to its inherent resilience, the distal end then expands, assuming its operative condition, and thereafter the sleeve may be extracted through the trocar, again by means of the manoeuvring rod 7.

Other means of causing contraction and expansion of the distal end are of course possible.

Figure 7:
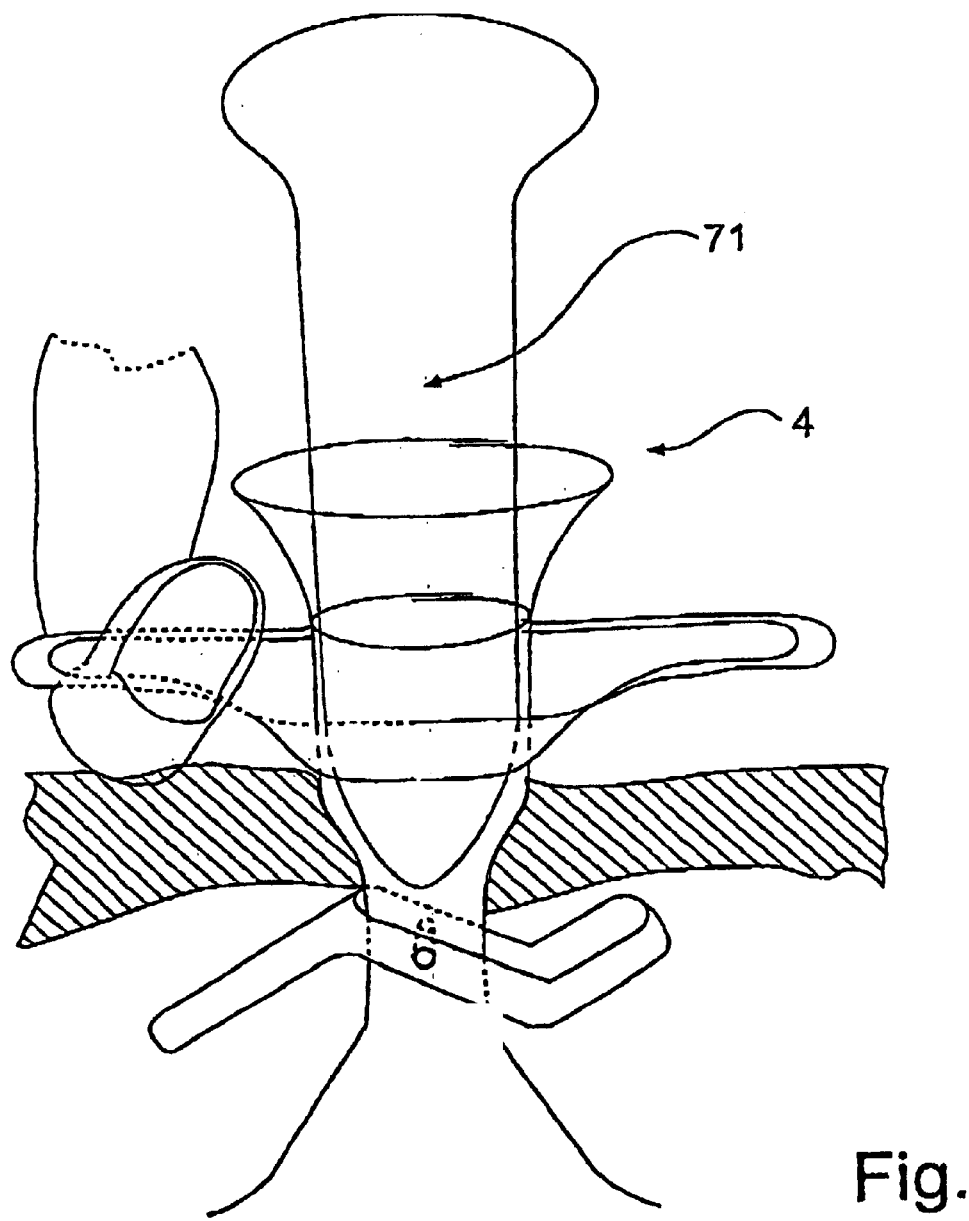
FIG. 7 is a view showing the use of a dilating member together with the device of FIG. 4.

The trocar formed with a dilatable sleeve is highly suitable in applications where so called dilation is employed. In such cases, a dilator 71 is formed through the preferably slightly funnel-shaped upper end of the trocar, as illustrated in FIG. 7. This is a considerably safer, more simple and less harmful way of providing a wider surgical orifice than widening such an orifice by means of a scalpel, which is the prevalent technique and often necessary when conventional trocars are used. The dilator is formed with a conically increasing circumference and when forced downwards, for instance with the aid of the grasping means 47 on the locking ring 46, the trocar and the surgical orifice are forced to dilate. In accordance with a preferred embodiment, the lower end of the obturator may be given a fusiform or similar configuration that may be used as the dilating means to widen the body orifice.

Figure 8:
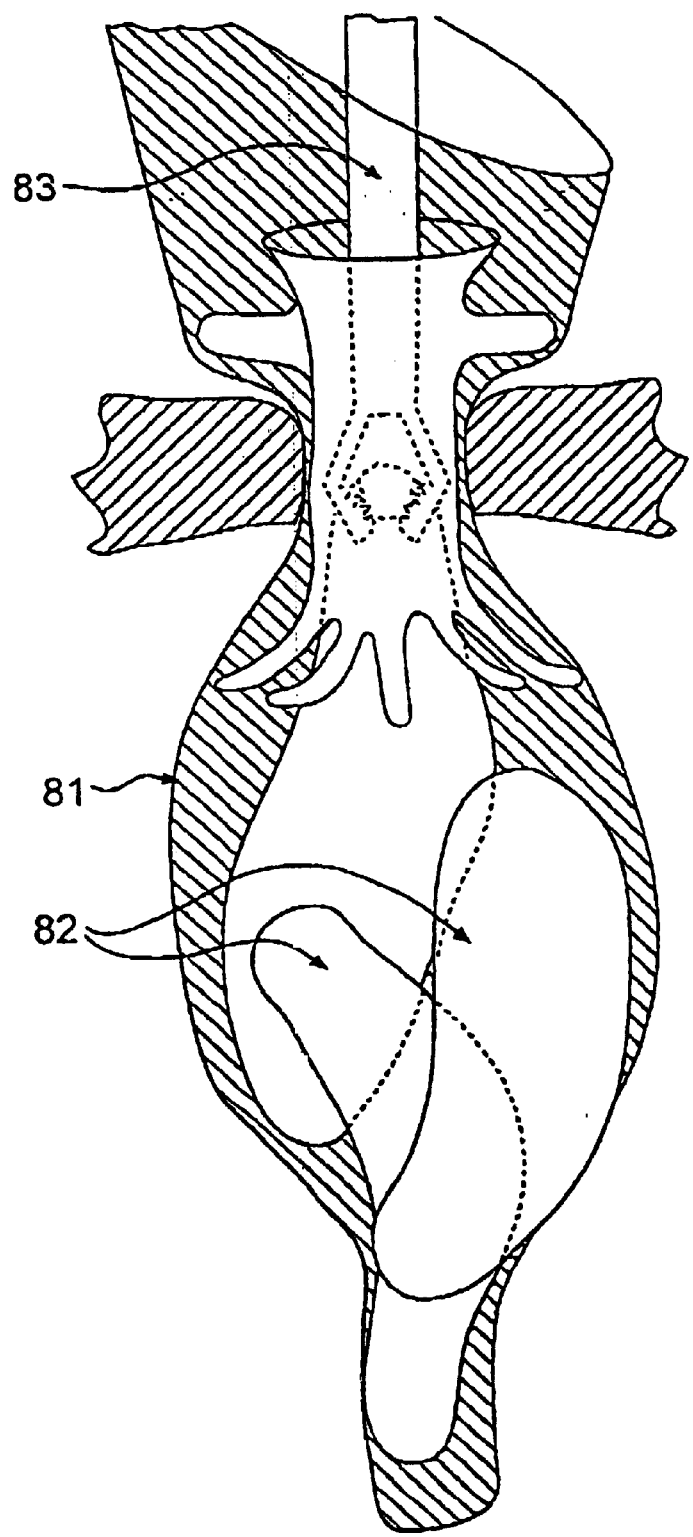
FIG. 8 is a view illustrating the use of a protective and collective bag together with the device of FIG. 4.

Furthermore, the trocar in accordance with the invention is suitable for use together with a protective and collection cover, such as a bag or the like, in which the specimens are collected before being extracted. One example of this situation is shown in FIG. 8. According to this example the bag 81 holding the specimen 82 has been arranged in such a manner that the trocar is located inside the bag. Of course, the trocar could equally well be located exteriorly of the bag. In use, the bag 81 facilitates extraction of the specimens by means of tongs 83 or similar implements by gathering and compressing the specimens. In addition, it protects surrounding organs.

The invention has been described above by means of embodiments thereof. The embodiments concern a trocar but it should be understood that other devices having a similar function could be configured in a corresponding manner and should be regarded to be embraced by the invention. Many other varieties and modifications of the invention are likewise possible. For example, the proximal end may be configured in many different ways. It is likewise possible to cause expansion of the distal end in other ways than shown, for example by means of pivotal rotating arms that may be controlled from the exterior and when rotating force the distal end outwards. Instead of being formed as a continuous tube, the sleeve could be configured as a lengthwise slitted tube, be made from joined-together ribbons or threads, or the like. The various details described in connection with the embodiments could also be combined in other ways than described above. These and other obvious varieties must be regarded to be within the scope of protection of the invention as the latter is defined in the appended claims.

What is claimed is:

1. A device intended to penetrate a body wall in endoscopic surgery to establish a passageway allowing insertion therethrough of surgical instruments, and comprising a tubular sleeve, which in use extends through said passageway and has one proximal and one distal end, wherein the distal end is arranged to be contracted such that its assumes transverse dimensions not exceeding the surgical orifice to allow said end to be introduced into said orifice, and thereafter to expand when applied in position such that it assumes downwards gradually increasing dimensions transversely exceeding the dimensions of the device at the place of the surgical orifice, whereby a funnel-shaped distal end is formed, and wherein at least the distal end is made from a resilient material which in itself tends to assume the expanded condition and wherein the distal end is arranged to be maintained in a contracted condition by an obturator to allow insertion of said distal end and by further insertion of the obturator release the distal end to expand, said obturator arranged to be extracted from the device from the proximal end.

2. A device as claimed in claim 1, wherein the sleeve comprises an continuous tube.

3. A device as claimed in claim 1, wherein said device is yieldable at least at its narrowest part and thus has variable transverse dimensions.

4. A device as claimed in claim 3, wherein the peripheral wall of said device is partitioned and arranged overlapping.

5. A device as claimed in claim 3, wherein it is made from a resilient material and tends to assume a predetermined normal position.

6. A device as claimed in claim 1, wherein at least on its inner face said device comprises a smooth material with low sliding resistance.

7. A device according to claim 1, said device further comprising a locking means to prevent said device, when in its inserted position, from being pulled upwards.

8. A device as claimed in claim 7, wherein said locking means may be shifted between an inner position, wherein it does not essentially protrude from the sleeve and an outer position, wherein at least partly it protrudes radially away from the sleeve.

9. A device intended to penetrate a body wall in endoscopic surgery to establish a passageway allowing insertion therethrough a passageway allowing insertion therethrough of surgical instruments, and comprising a tubular sleeve, which in use extends through said passageway and has one proximal and one distal end, wherein the distal end is arranged to be contracted such that it assumes transverse dimensions not exceeding the surgical orifice to allow said end to be introduced into said orifice, and thereafter to expand when applied in position such that it assumes downwards gradually increasing dimensions transversely exceeding the dimensions of the device at the place of the surgical orifice, whereby a funnel-shaped distal end is formed, and said device is yieldable at least at its narrowest part and the peripheral wall of said device is partitioned and arranged overlapping, wherein the device has variable transverse dimensions.

10. A device as claimed in claim 9, wherein the sleeve comprises an continuous tube.

11. A device as claimed in claim 9, wherein the distal end is arranged to be maintained in a contracted condition by an obturator to allow insertion of said distal end, said obturator arranged to be extracted from the device from the proximal end.

12. A device as claimed in claim 9, wherein at least the distal end is made from a resilient material which in itself tends to assume the expanded condition.

13. A device as claimed in claim 9, wherein it is made from a resilient material and tends to assume a predetermined normal position.

14. A device as claimed in claim 9, wherein at least on its inner face said device comprises a smooth material with low sliding resistance.

15. A device according to claim 9, said device further comprising a locking means to prevent said device, when in its inserted position, from being pulled upwards.

16. A device as claimed in claim 15, wherein said locking means may be shifted between an inner position, wherein it does not essentially protrude from the sleeve and an outer position, wherein at least partly it protrudes radially away from the sleeve.

17. A device intended to penetrate a body wall in endoscopic surgery to establish a passageway allowing insertion therethrough of surgical instruments, and comprising a tubular sleeve, which in use extends through said passageway and has one proximal and one distal end, wherein the distal end is arranged to be contracted such that it assumes transverse dimensions not exceeding the surgical orifice to allow said end to be introduced into said orifice, and thereafter to expand when applied in position such that it assumes downwards gradually increasing dimensions transversely exceeding the dimensions of the device at the place of the surgical orifice, whereby a funnel-shaped distal end is formed, said device further comprising a locking means to prevent said device, when in its inserted position, from being pulled upwards, wherein said locking means may be shifted between an inner position, wherein it does not essentially protrude from the sleeve and an outer position, wherein at least partly it protrudes radially away form the sleeve.

18. A device as claimed in claim 17, wherein the sleeve comprises an continuous tube.

19. A device as claimed in claim 17, wherein the distal end is arranged to be maintained in a contracted condition by an obturator to allow insertion of said distal end, said obturator arranged to be extracted from the device from the proximal end.

20. A device as claimed in claim 17, wherein at least the distal end is made from a resilient material which in itself tends to assume the expanded condition.

21. A device as claimed in claim 17, wherein said device is yieldable at least at its narrowest part and thus has variable transverse dimensions.

22. A device as claimed in claim 21, wherein the peripheral wall of said device is partitioned and arranged overlapping.

23. A device as claimed in claim 21, wherein it is made from a resilient material and tends to assume a predetermined normal position.

24. A device as claimed in claim 17, wherein at least on its inner face said device comprises a smooth material with low sliding resistance.

25. A device as claimed in claim 1, wherein at least on its inner face said device comprises a smooth plastic material with low sliding resistance.

26. A device as claimed in claim 9, wherein at least on its inner face said device comprises a smooth plastic material with low sliding resistance.

27. A device as claimed in claim 17 wherein at least on its inner face said device comprises a smooth material with low sliding resistance.

* * * * *